US012799058B2

(12) United States Patent
Leyshon et al.

(10) Patent No.: US 12,799,058 B2
(45) Date of Patent: Nov. 17, 2026

(54) USE OF CARBON DIOXIDE TO IMPROVE CAUSTIC WASHING OF ALKYLENE OXIDE / ALKENYL BENZENE MONOMER STREAMS

(71) Applicant: Lyondell Chemical Technology, L.P., Houston, TX (US)

(72) Inventors: David W. Leyshon, West Chester, PA (US); Sandor Nagy, Seabrook, TX (US); Elizabeth I. Ross-Medgaarden, Humble, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 705 days.

(21) Appl. No.: 18/303,844

(22) Filed: Apr. 20, 2023

(65) Prior Publication Data

US 2023/0339832 A1 Oct. 26, 2023

Related U.S. Application Data

(60) Provisional application No. 63/333,409, filed on Apr. 21, 2022.

(51) Int. Cl.
*C07C 39/04* (2006.01)
*C07C 7/10* (2006.01)
*C07C 15/46* (2006.01)

(52) U.S. Cl.
CPC .................................... *C07C 39/04* (2013.01)

(58) Field of Classification Search
CPC ........... C07C 39/04; C07C 7/10; C07C 15/46; C07D 301/32
See application file for complete search history.

(56) References Cited

U.S. PATENT DOCUMENTS

| | | | | |
|---|---|---|---|---|
| 3,351,635 | A | 11/1967 | Kollar | |
| 3,439,001 | A | 4/1969 | Pell et al. | |
| 4,066,706 | A | 1/1978 | Schmidt | |
| 10,710,004 | B2 * | 7/2020 | Nagy | B01D 11/0484 |
| 2018/0221787 | A1 | 8/2018 | Nagy et al. | |
| 2018/0312764 | A1 | 11/2018 | Nagy et al. | |

OTHER PUBLICATIONS

International Search Report and Written Opinion for PCT/US2023/019221 mailed Oct. 26, 2023.

* cited by examiner

*Primary Examiner* — Sikarl A Witherspoon

(57) ABSTRACT

A method for removing metal salts from alkylaromatic oxidate streams used for alkene oxide production, or used in the co-production of propylene oxide and styrene monomer ("POSM"), and methods for caustic washing of oxidate streams formed in these processes. The concentration of metal salts carried over from a caustic washing may be reduced by washing the organic phase resulting from the caustic wash with water in the presence of carbon dioxide ($CO_2$). The $CO_2$ may be provided in any form, such as gaseous $CO_2$, dry ice, carbonated water, supercritical (liquid) $CO_2$, or any other suitable form.

20 Claims, 3 Drawing Sheets

USE OF CARBON DIOXIDE TO IMPROVE CAUSTIC WASHING OF ALKYLENE OXIDE / ALKENYL BENZENE MONOMER STREAMS

CROSS-REFERENCE TO RELATED APPLICATIONS

The application claims the benefit of priority to U.S. Provisional Patent Application No. 63/333,409, filed on Apr. 21, 2022, which is incorporated herein by reference in its entirety.

FIELD OF THE INVENTION

This disclosure relates to the co-production of propylene oxide and styrene monomer from the oxidation of ethyl benzene and to the caustic washing of POSM streams.

BACKGROUND

The co-production of propylene oxide and styrene monomer (the "POSM process") involves the oxidation of ethyl benzene with molecular oxygen to form ethyl benzene hydroperoxide, and the catalytic reaction of the ethyl benzene hydroperoxide with propylene to form propylene oxide and 1-phenyl ethanol. The 1-phenyl ethanol is subsequently dehydrated to produce styrene monomer.

The oxidate stream resulting from the oxidation of ethyl benzene with molecular oxygen to form ethyl benzene hydroperoxide (also, (1-hydroperoxyethyl)benzene) can also contain undesirable compounds. For example, the oxidate stream containing ethyl benzene hydroperoxide can contain acids such as carboxylic acids and/or phenols, which may interfere with the POSM process when ethyl benzene is recycled. To remedy these undesired phenols and/or acids, including, e.g., carboxylic acids, one or more caustic washings (aqueous NaOH) of POSM streams can be employed to reduce the acidic characteristics of the oxidate stream arising from these compounds which would otherwise impede the process. However, caustic washing leaves residual alkali metal (for example, sodium) salts in the process stream, which are difficult to remove and which can poison catalysts and cause fouling.

Therefore, what are needed are new methods for caustic washing of POSM streams, which can address these issues and provide improvements in removing such salts.

BRIEF SUMMARY

This disclosure provides processes for treating an alkylaromatic oxidate stream used for alkene oxide production, the process including: providing an alkylaromatic oxidate stream including: (i) an alkylaromatic hydroperoxide, (ii) at least one undesired compound, and (iii) an organic solvent; contacting the alkylaromatic oxidate stream with an aqueous alkali solution to form a mixture, followed by separating the mixture into an aqueous phase and an organic phase; and subjecting the organic phase to one or more washing and separating cycles, each cycle including washing the organic phase with water to form a subsequent mixture followed by separating the subsequent mixture into a subsequent aqueous phase and a subsequent organic phase, wherein at least one of the washing and separating cycles includes washing the organic phase or any subsequent organic phase with water in the presence of carbon dioxide.

In another aspect, this disclosure further provides processes for removing sodium salts formed in the co-production of propylene oxide and styrene monomer, the process including: providing an ethylbenzene oxidate stream including: (i) ethylbenzene hydroperoxide, (ii) at least one undesired compound, and (iii) an organic solvent; contacting the ethylbenzene oxidate stream with an aqueous sodium hydroxide solution to form a mixture, followed by separating the mixture into an aqueous phase and an organic phase; subjecting the organic phase to one or more washing and separating cycles, each cycle includes washing the organic phase with water to form a subsequent mixture followed by separating the subsequent mixture into a subsequent aqueous phase and a subsequent organic phase, wherein at least one of the washing and separating cycles includes washing the organic phase or any subsequent organic phase with water in the presence of carbon dioxide; and directing a portion of any subsequent organic phase to a reactor.

According to another aspect, the processes for removing metal salts from an alkylaromatic oxidate stream can be integrated into a process for the co-production of an alkene oxide, for example propylene oxide, and the alkenylaromatic monomer styrene. For example, there are provided processes for the co-production of an alkene oxide and styrene monomer, the processes including: contacting molecular oxygen with ethylbenzene to form an oxidate stream including ethylbenzene hydroperoxide and at least one undesired compound; contacting the oxidate stream with an aqueous alkali solution to form a mixture, followed by separating the mixture into an aqueous phase and an organic phase including ethylbenzene hydroperoxide; subjecting the organic phase to one or more washing and separating cycles, each cycle comprising washing the organic phase with water to form a subsequent mixture followed by separating the subsequent mixture into a subsequent aqueous phase and a subsequent organic phase including ethylbenzene hydroperoxide; contacting the ethylbenzene hydroperoxide of the subsequent organic phase with an alkene in the presence of a catalyst to form a reaction mixture including an alkene oxide and 1-phenylethanol; and dehydrating the 1-phenylethanol of the reaction mixture to provide styrene; wherein at least one of the washing and separating cycles includes washing the organic phase or any subsequent organic phase with water in the presence of carbon dioxide.

In any of the foregoing aspects, the carbon dioxide can be provided in any form. For example, in some embodiments, the $CO_2$ can be provided in the form of gaseous $CO_2$, dry ice, carbonated water, supercritical (liquid) $CO_2$, or other forms. Treating the alkylaromatic oxidate stream in this manner reduces the concentration of metal salts in the stream to be used in subsequent reactions in the POSM process.

While multiple embodiments are disclosed, other embodiments will become apparent to those skilled in the art from the following detailed description. As will be apparent, certain embodiments, as disclosed herein, are capable of modifications in various aspects without departing from the spirit and scope of the claims as presented herein. Accordingly, the detailed description hereinbelow is to be regarded as illustrative in nature and not restrictive.

BRIEF DESCRIPTION OF THE DRAWINGS

The following figures illustrate embodiments of the subject matter disclosed herein. The claimed subject matter may be understood by reference to the following description taken in conjunction with the accompanying figures, in which like reference numerals identify like elements, and in which:

DETAILED DESCRIPTION

Figure 1:
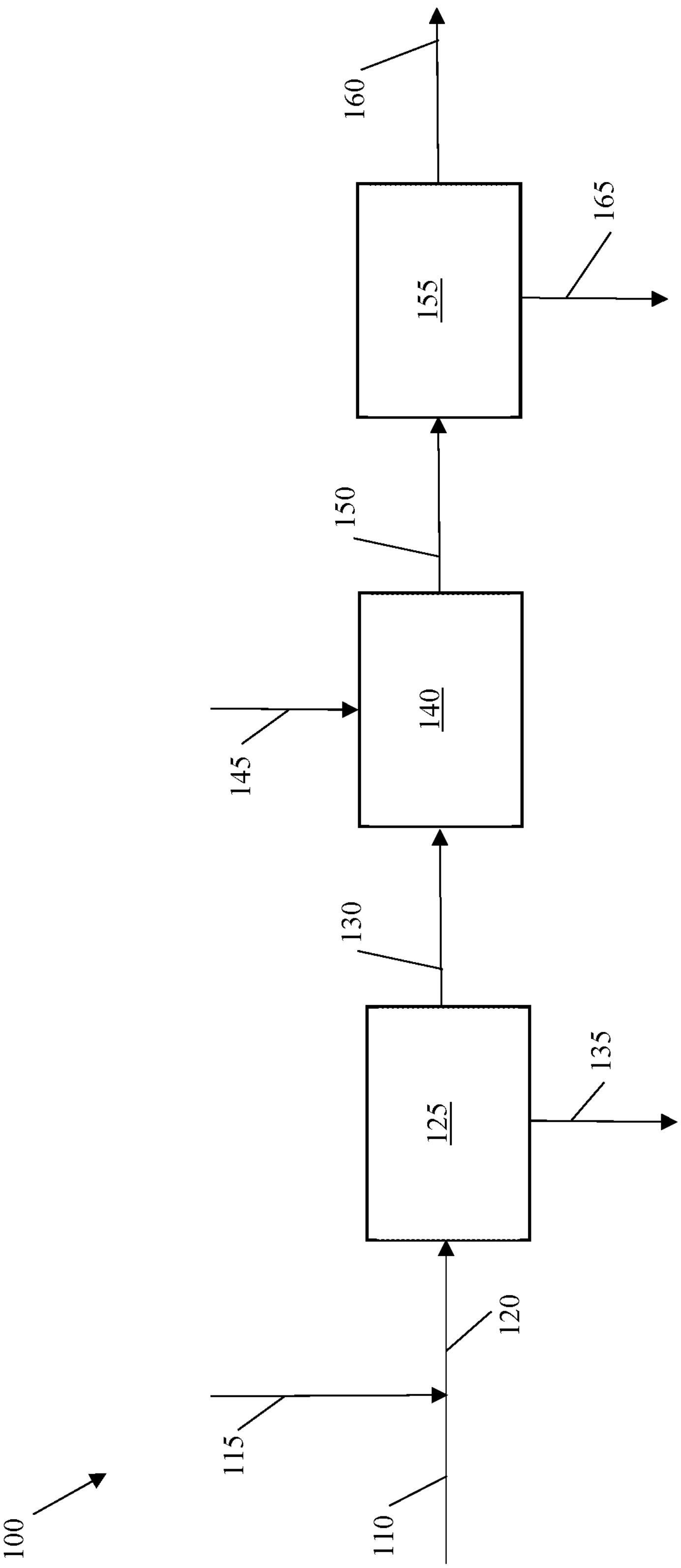
FIG. 1 is a schematic of a system for treating an alkylaromatic oxidate stream used for alkene oxide production according to an embodiment of this disclosure.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments are possible. This description is not to be taken in a limiting sense, but rather made merely for the purpose of describing the general principles of the implementations. The scope of the described implementations should be ascertained with reference to the issued claims.

The following patents disclose background information related to the present disclosure, and each of these following patents is incorporated herein by reference in their entireties. A basic patent describing the co-production of propylene oxide and styrene monomer (the "POSM" process) is U.S. Pat. No. 3,351,635, which includes suitable conditions and catalysts for this process and procedures for the dehydration of the 1-phenyl ethanol stream to styrene monomer. U.S. Pat. No. 4,066,706 also provides a detailed description of this process. The use of caustic treatment to reduce the acidic components of the oxidate stream is described in, for example, U.S. Pat. No. 3,439,001. These references are incorporated herein by reference in their entireties.

In the POSM process, ethylbenzene is oxidized with molecular oxygen at elevated temperatures to form a reaction mixture or "oxidate stream" containing ethylbenzene hydroperoxide. The ethylbenzene hydroperoxide in the reaction mixture is employed in the epoxidation of an olefin such as propylene, during which the ethylbenzene hydroperoxide is converted to alpha phenyl ethanol. Subsequent dehydration of the alpha phenyl ethanol provides styrene monomer.

Generally one or more base treatment steps can be employed in order to reduce the acidic characteristics of various streams. For example, treating the oxidate stream formed from the molecular oxidation of ethyl benzene with caustic (sodium hydroxide) can remove undesirable compounds, e.g., acids, phenols, and carboxylic acids. Other alkali metal hydroxides such as potassium hydroxide can be used. However, this process can also result in undesirable amounts of metal salts such as sodium salts being carried over to subsequent steps in the POSM process, which may result in fouling or poisoning the catalysts. It has been surprisingly found that adding $CO_2$ can improve the removal of alkali metal salts from the organic phase. This improvement can result in less water being needed to achieve the same level of alkali metal salt removal as obtained without the use of $CO_2$, reduce fouling, and improve catalyst life downstream.

Therefore, in one aspect, the present disclosure provides processes for removing metal salts from an alkylaromatic oxidate stream used for alkene oxide production. For example, there is provided a process for treating an alkylaromatic oxidate stream used for alkene oxide production, the process comprising: providing an alkylaromatic oxidate stream comprising (i) an alkylaromatic hydroperoxide, (ii) at least one undesired compound, and (iii) an organic solvent; contacting the alkylaromatic oxidate stream with an aqueous alkali solution to form a mixture, followed by separating the mixture into an aqueous phase and an organic phase; and subjecting the organic phase to one or more washing and separating cycles, each cycle comprising washing the organic phase with water to form a subsequent mixture followed by separating the subsequent mixture into a subsequent aqueous phase and a subsequent organic phase, wherein at least one of the washing and separating cycles comprises washing the organic phase or any subsequent organic phase with water in the presence of carbon dioxide.

As used herein, "in the presence of carbon dioxide", or variants thereof, refers to any amount, concentration or quantity of carbon dioxide added to any portion of a washing and separation cycle.

As used herein, "in the absence of carbon dioxide", or variants thereof, refers to any amount, concentration or quantity of carbon dioxide in excess of that which naturally occurs in water at the conditions that the washing portion of a washing and separating cycle occurs.

System 100 of FIG. 1 comprises first separations unit 125, wash unit 140 and second separations unit 155. An alkylaromatic hydroperoxide stream 110 is contacted with an aqueous alkali stream 115 to form first mixed stream 120. First mixed stream 120 comprises a mixture of organic and aqueous components. First mixed stream 120 enters first separations unit 125 wherein the mixture is separated into a first aqueous phase and a first organic phase. The first aqueous phase is removed from separations unit 125 via line 135. The first organic phase is removed from first separations unit 125 and transported to the first wash unit 140 via line 130. In the first wash unit 140, the first organic phase is contacted with water and carbon dioxide 145 to form second mixed stream 150. Second mixed stream 150 comprises a second mixture of organic and aqueous components. Second mixed stream 150 enters second separations unit 155 wherein the second mixture is separated into a second aqueous phase and a second organic phase. The second aqueous phase is removed from second separations unit 155 via line 165. The second organic phase is removed from second separations unit 155 via line 160. The concentration of alkali metal salt in the second organic phase in line 160 is less than the concentration of alkali metal salt in the second organic phase in line 130.

In some embodiments, the second organic phase may be subjected to one or more additional wash cycles. In such embodiments, the system comprises more than one wash unit and separations unit pair in series. For example, line 160 may deliver the second organic phase to a second wash unit where the second organic phase is again washed with water and carbon dioxide to form a third mixed stream that is subsequently separated into a third aqueous stream and a third organic phase in a third separations unit.

In some embodiments having multiple wash cycles, all of the wash cycles include contacting the organic phase with carbon dioxide. In some embodiments having multiple wash cycles, only one of the wash cycles includes contacting the organic phase with carbon dioxide (i.e., in other words, only water is used in the cycles lacking carbon dioxide). In some embodiments having multiple wash cycles, all but one of the wash cycles include contacting the organic phase with carbon dioxide. In some embodiments having multiple wash cycles including carbon dioxide, the concentration of carbon dioxide in each wash cycle may be different than or the same as the concentration of carbon dioxide in any other wash cycle.

In some embodiments the final organic phase, be it the second organic phase in an embodiment having a single wash cycle or the fourth organic phase in an embodiment with three wash cycles, is directed to a reactor.

Figure 2:
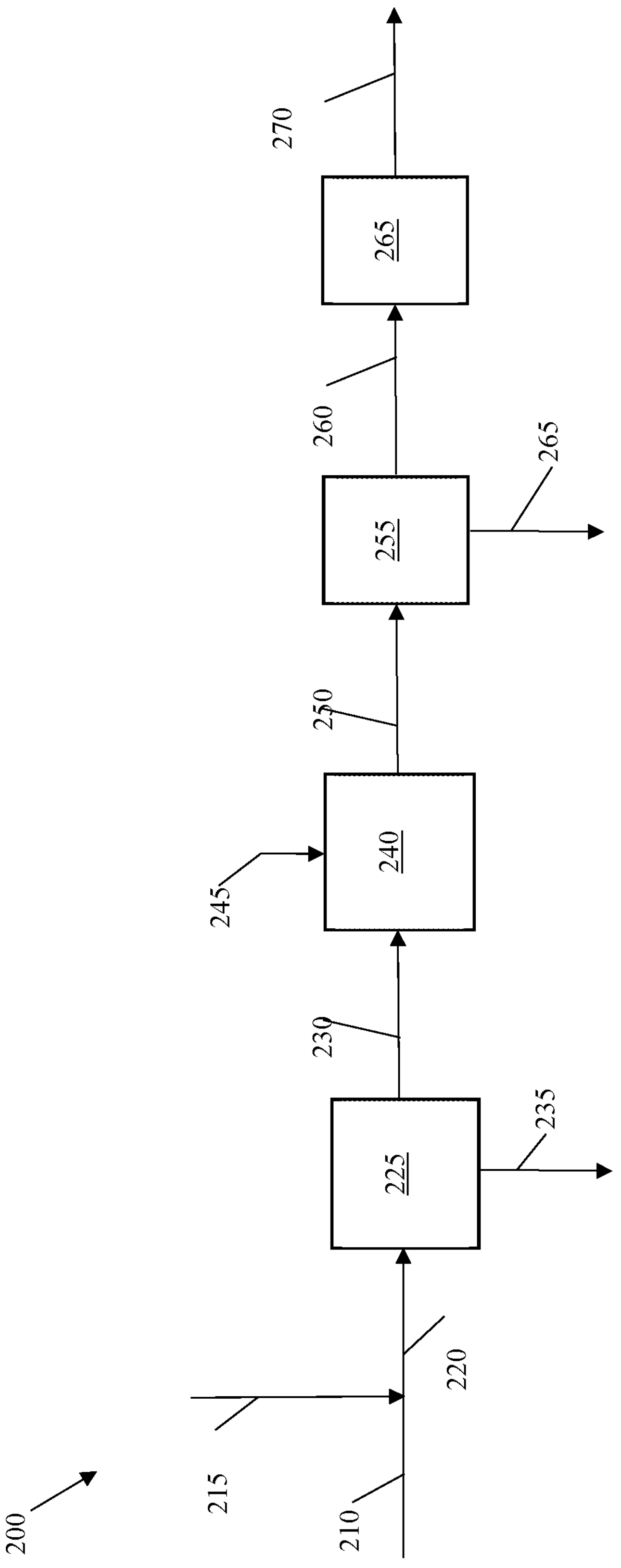
FIG. 2 is a schematic of a system for removing sodium salts formed in the co-production of propylene oxide and styrene monomer according to an embodiment of this disclosure.

System 200 of FIG. 2 comprises first separations unit 225, wash unit 240, second separations unit 255, and reactor 265. An alkylaromatic hydroperoxide stream 210 is contacted with an aqueous alkali stream 215 to form first mixed stream 220. First mixed stream 220 comprises a mixture of organic and aqueous components. First mixed stream 220 enters first separations unit 225 wherein the mixture is separated into a first aqueous phase and a first organic phase. The first aqueous phase is removed from separations unit 225 via line 235. The first organic phase is removed from first separations unit 225 and transported to the first wash unit 240 via line 230. In the first wash unit 240, the first organic phase is contacted with water and carbon dioxide 245 to form second mixed stream 250. Second mixed stream 250 comprises a second mixture of organic and aqueous components. Second mixed stream 250 enters second separations unit 255 wherein the second mixture is separated into a second aqueous phase and a second organic phase. The second aqueous phase is removed from second separations unit 255 via line 265. The second organic phase is removed from second separations unit 255 via line 260. The concentration of alkali metal salt in the second organic phase in line 260 is less than the concentration of alkali metal salt in the second organic phase in line 230. Line 260 transports the second organic phase to reactor 265. In reactor 265 the second organic phase reacts in the presence of a catalyst with an olefin to produce a product stream 270 comprising methylbenzyl alcohol and alkene oxide.

In some embodiments, the second organic phase may be subjected to one or more additional wash cycles. In such embodiments, the system comprises more than one wash unit and separations unit pair in series. For example, line 260 may deliver the second organic phase to a second wash unit where the second organic phase is again washed with water and carbon dioxide to form a third mixed stream that is subsequently separated into a third aqueous stream and a third organic phase in a third separations unit.

In some embodiments having multiple wash cycles, all of the wash cycles include contacting the organic phase with carbon dioxide. In some embodiments having multiple wash cycles, only one of the wash cycles includes contacting the organic phase with carbon dioxide (i.e., in other words, the other washes are conducted in the absence of carbon dioxide). In some embodiments having multiple wash cycles, all but one of the wash cycles include contacting the organic phase with carbon dioxide. In some embodiments having multiple wash cycles including carbon dioxide, the concentration of carbon dioxide in each wash cycle may be different than or the same as the concentration of carbon dioxide in any other wash cycle. In some embodiments having multiple wash cycles, the organic phase exiting the separations unit of the last wash cycle is directed to reactor 265.

Figure 3:
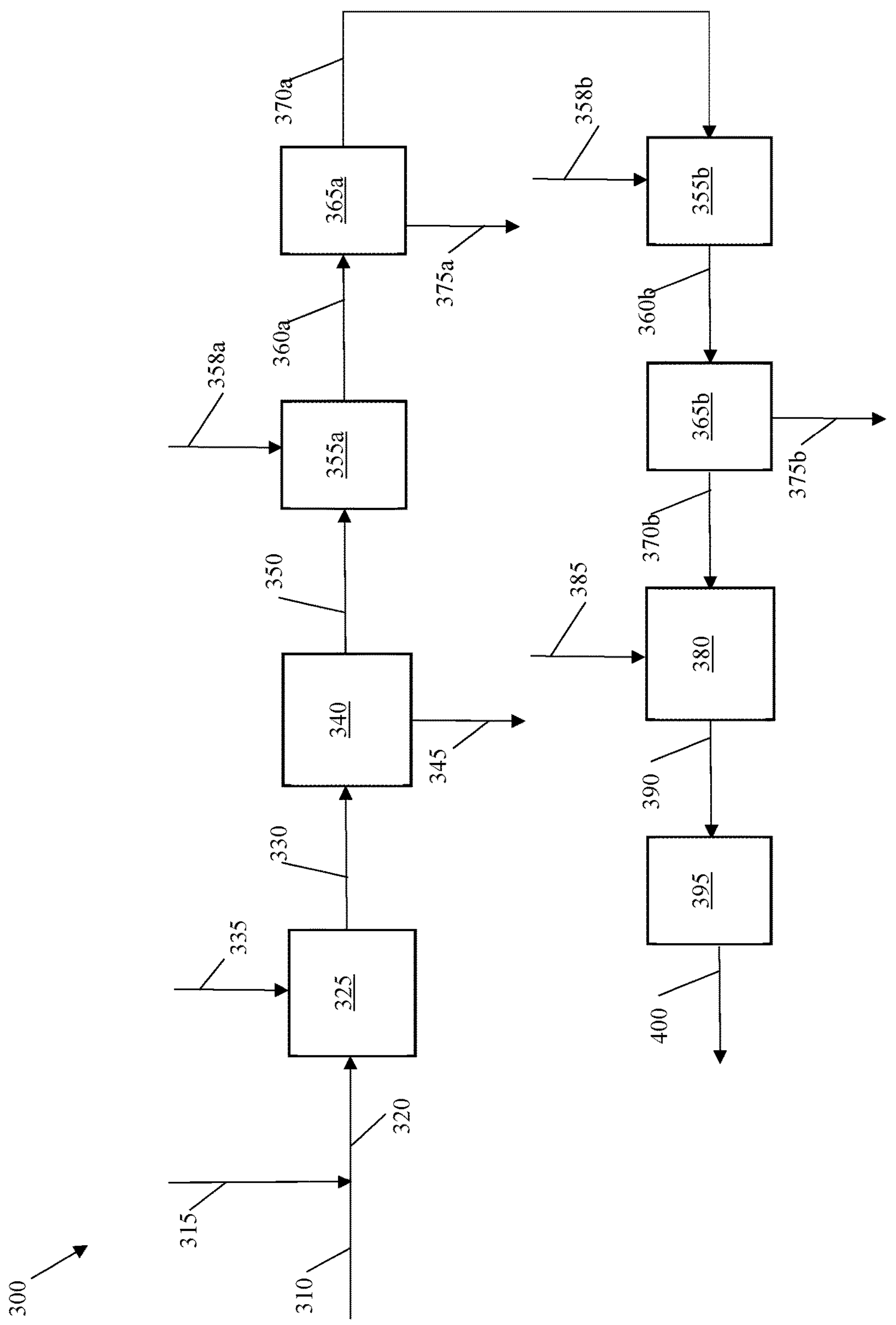
FIG. 3 is a schematic of a system for removing metal salts from an alkylaromatic oxidate stream can be integrated into a process for the co-production of an alkene oxide according to an embodiment of this disclosure.

System 300 of FIG. 3 comprises a first mixing vessel 325, first separations unit 340, first wash unit 355*a*, second separations unit 365*a*, second wash unit 355*b*, third separations unit 365*b*, reactor 380 and dehydration unit 395. An ethylbenzene stream 310 is contacted with molecular oxygen stream 315 to form an oxidate stream 320 comprising ethylbenzene hydroperoxide. Oxidate stream 320 enters first mixing vessel 325 where it is mixed with an aqueous alkali solution 335 to provide a first mixed stream 330 comprising a mixture of organic and aqueous components. First mixed stream 330 is separated into a first aqueous phase and a first organic phase in first separations unit 340. The first aqueous phase is removed as stream 345. The first organic phase is removed from first separations unit 340 as stream 350 and delivered to first wash unit 355*a*. In first wash unit 355*a*, the received first organic phase is washed with water and carbon dioxide 358*a* to provide second mixed stream 360*a*. Second mixed stream 360*a* is separated into a second aqueous phase and a second organic phase in second separations unit 365*a*. The second aqueous phase is removed as stream 375*a*. Second organic phase passes via line 370*a* to second wash unit 355*b*. In second wash unit 355*b*, the received second organic phase is washed with water and carbon dioxide 358*b* to provide third mixed stream 360*b*. Third mixed stream 360*b* is separated into a third aqueous phase and a third organic phase in third separations unit 365*b*. The third aqueous phase is removed as stream 375*b*. The third organic phase is transported via line 370*b* to reactor 380 where the ethylbenzene hydroperoxide of the third organic phase reacts with an alkene supplied via line 385 forming a reaction mixture comprising an alkene oxide and 1-phenylethanol. The 1-phenylethanol is transported to dehydration unit 395 where it is dehydrated to styrene providing styrene stream 400.

In some embodiments, each wash cycle includes contacting the received organic phase with carbon dioxide. In some embodiments, the amount of carbon dioxide used in a wash cycle may be different (e.g., more than or less than) than the amount of carbon dioxide used in a subsequent wash cycle. In some embodiments, only one of the wash cycles includes contacting the organic phase with carbon dioxide while the others are conducted in the absence of carbon dioxide. For example, with reference to FIG. 3, in some embodiments stream 358*a* may comprise water only (i.e., in the absence of carbon dioxide) while stream 358*b* may comprise water and carbon dioxide. In other embodiments, stream 358*a* may comprise water and carbon dioxide while stream 358*b* is water only (i.e., in the absence of carbon dioxide).

In embodiments, the concentration of the alkylaromatic hydroperoxide in the alkylaromatic oxidate stream can be from about 1.0 wt. % to about 40 wt. %. The concentration of the alkylaromatic hydroperoxide in the alkylaromatic oxidate stream can be from about 5 wt. % to about 20 wt. %. The concentration of the alkylaromatic hydroperoxide in the alkylaromatic oxidate stream also can be from about 5 wt. % to about 15 wt. %.

In embodiments, the aqueous alkali solution comprises an alkali metal hydroxide. In embodiments, the alkali metal hydroxide is sodium hydroxide or potassium hydroxide.

In embodiments, the alkylaromatic oxidate stream can be an ethylbenzene oxidate stream comprising ethylbenzene hydroperoxide. In such embodiments, the concentration of ethylbenzene hydroperoxide in the ethylbenzene oxidate stream can be from about 1.0 wt. % to about 40 wt. %, from about 5 wt. % to about 20 wt. %, or from about 5 wt. % to about 15 wt. %.

In another aspect, the alkylaromatic oxidate stream comprising ethylbenzene hydroperoxide can be used for the production of propylene oxide and styrene monomer. As such, the ethylbenzene hydroperoxide of the ethylbenzene oxidate stream can be reacted with propylene in the presence of a catalyst to form a reaction mixture comprising propylene oxide and 1-phenylethanol. The 1-phenylethanol can subsequently be dehydrated to form styrene monomer. In another aspect, the alkylaromatic oxidate stream can be a cumene oxidate stream.

In embodiments, the ethylbenzene hydroperoxide recovered from the ethylbenzene oxidate stream also can be reacted with alkenes other than propylene in the presence of a catalyst to form a reaction mixture comprising an alkene oxide and 1-phenylethanol. For example, the alkene can be selected from or can comprise ethylene, propylene, normal butene, pentenes, methyl pentenes, normal hexene, octenes, dodecenes, cyclohexene, methyl cyclohexenes, phenyl cyclohexenes, butadiene, styrene, methyl styrene, vinyl toluene, vinylcyclohexane, and the like.

When a mixture, organic phase or subsequent organic phase, as in the case of multiple cycles as described further below, is washed with water to form a subsequent mixture followed by separating the subsequent mixture into a subsequent aqueous and a subsequent organic phase, this can be referred to as a washing and separating cycle. In this aspect, the disclosed process can comprise one, two, three, four, five, six, seven, eight, nine, ten, or more washing and separating cycles. Carbon dioxide can be used in any or all of the washing and separating cycles. In embodiments, the disclosed process can comprise two or more washing and separating cycles with water in the absence of carbon dioxide and any or all of the subsequent washing and separating cycles can comprise washing the organic phase with water in the presence of carbon dioxide. For example, the disclosed process can comprise two washing and separating cycles, wherein the first washing and separating cycle comprises washing the organic phase with water in the absence of carbon dioxide, and washing the subsequent organic phase in the presence of carbon dioxide. In some embodiments, only the last wash of the washing and separating cycle is conducted in the presence of carbon dioxide.

The carbon dioxide may be present in an amount effective to reduce the concentration of alkali metals from the organic phase or subsequent organic phase below a target value. In embodiments, the carbon dioxide may be introduced as a gas into a vessel through which the mixture, organic phase or subsequent organic phase passes under conditions effective reduce the concentration of the alkali metal below a target value. In embodiments, the target value may be selected by the operator based on one or more factors and the quantity of carbon dioxide adjusted to achieve the desired result. For example, the sensitivity of the catalyst to alkali metal concentration in the organic phase may determine the target value. In embodiments, the target value may be any value, including 500 ppm, 100 ppm, 50 ppm, 10 ppm, 5 ppm, 1 ppm, 0.5 ppm, 0.4 ppm, 0.3 ppm, 0.2 ppm, 0.1 ppm or 0.01 ppm.

In some embodiments, the carbon dioxide may be introduced as a substantially pure gas or as a mixed gas phase comprising one or more diluent or carrier gas inert to the washing and separation operation. In some embodiments, the carbon dioxide may be added to the mixture, organic phase, or subsequent organic phase at any volumetric rate, including 50 liters per minute, 30 liters per minute, 20 liters per minute, 10 liters per minute, 6 liters per minute, 1 liter per minute, or less, depending on the volume of mixture, organic phase or subsequent organic phase being so treated. In some embodiments, the ratio of carbon dioxide to the alkylaromatic oxidate mixture, on a mass basis, is from 1:25 to 1:300. In some embodiments, the ratio of carbon dioxide to the alkylaromatic oxidate mixture is from 1:75 to 1:200. In some embodiments, the ratio of carbon dioxide to the alkylaromatic oxidate mixture is from 1:100 to 1:175. In some embodiments, the ratio of carbon dioxide to the alkylaromatic oxidate mixture is from 1:150 to 1:250. In some embodiments, the ratio of carbon dioxide to the alkylaromatic oxidate mixture is from 1:150 to 1:300. In some embodiments, the ratio of carbon dioxide to the alkylaromatic oxidate mixture is from 1:100 to 1:300. In some embodiments, the ratio of carbon dioxide to the alkylaromatic oxidate mixture is from 1:75 to 1:300. In some embodiments, the ratio of carbon dioxide to the alkylaromatic oxidate mixture is from 1:200 to 1:300.

In another aspect, the carbon dioxide ($CO_2$) used in the washing portion of a washing and separation cycle can be provided in the form of gaseous $CO_2$, dry ice, carbonated water, or supercritical (liquid) $CO_2$. When more than one washing in the presence of $CO_2$ operation is employed, the form of the $CO_2$ can be the same or different in the steps, and the forms can be selected independently of each other.

The oxidate stream to be base-treated and subsequently washed with water in the presence of $CO_2$ can contain at least one undesired compound. The undesired compound may include an acid, a phenol, and/or a carboxylic acid. Reference to a phenol is intended to include phenol itself and substituted phenols. Following the aqueous base treatment, the concentration of the undesired compound in the organic phase separated from the aqueous base (for example, alkali metal hydroxide) treatment may be less than the corresponding concentration in the oxidate stream to be base-treated. Similarly, following the washing step in the presence of $CO_2$, the concentration of the alkali metal itself in the subsequent organic phase may be less than the concentration in the organic phase separated from the aqueous alkali metal hydroxide treatment.

In a further aspect, the concentration of alkali metal in the subsequent organic phase resulting from washing the organic phase one or more times with water to form a subsequent mixture where one of the washes is conducted in the presence of carbon dioxide, may be less than the concentration of alkali metal in the subsequent organic phase when the washing and separating cycle are conducted without the addition of carbon dioxide.

The oxidate stream such as the alkylaromatic oxidate stream can comprise (i) an alkylaromatic hydroperoxide, (ii) an undesired compound, and (iii) an organic solvent. The organic solvent can be an aliphatic or an aromatic solvent. For example, solvents can include a $C_6$ to $C_{12}$ or heavier aliphatic solvent or mixtures of aliphatic compounds. Solvents also can include a benzene, toluene, xylenes, and heavier aromatic solvents, including mixtures thereof. The undesired compound can include: an undesired acid, an undesired phenol, and/or an undesired carboxylic acid.

When the oxidate stream is contacted with an aqueous alkali solution, any alkali metal hydroxide can be used to form the aqueous alkali solution. For example, the aqueous alkali solution can comprise sodium hydroxide or potassium hydroxide. Other aqueous alkali metal hydroxides can be used, but they may be either less basic (for example, lithium hydroxide) or very expensive (rubidium hydroxide, cesium hydroxide), therefore, sodium hydroxide may be the most commonly employed.

In the step of contacting the oxidate stream one or more times with an aqueous alkali solution to base-treat the oxidate stream, the alkali metal hydroxide can be used in any concentration that reduces the concentration of the undesirable compounds, including acids, phenols, and/or carboxylic or other acids. For example, the concentration of the alkali metal hydroxide in the aqueous alkali solution to base-treat the oxidate stream can be from about 0.5 wt. % to about 50 wt. %. The concentration of the alkali metal hydroxide in the aqueous alkali solution also can be from about 0.75 wt. % to about 25 wt. %, or from about 1 wt. % to about 10 wt. %. In another aspect, the concentration of the alkali metal hydroxide in the aqueous alkali solution can be about 0.5 wt. %, about 0.75 wt. %, about 1 wt. %, about 2 wt. %, about 3 wt. %, about 4 wt. %, about 5 wt. %, about 7.5 wt. %, about 10 wt. %, about 15 wt. %, or about 20 wt. %.

In embodiments, the step of contacting the oxidate stream with an aqueous alkali solution, the one or more washing and separating cycles, or both can be carried out at a temperature of from about 10° C. to about 150° C. In an aspect, these steps can independently be conducted at a temperature of from about 20° C. to about 95° C. For example, the contacting step and the one or more washing and separating cycles can be conducted at a temperature of about 10° C., about 20° C., about 30° C., about 40° C., about 50° C., about 60° C., about 70° C., about 75° C., about 80° C., about 85° C., about 90° C., about 95° C., about 100° C., about 105° C., about 110° C., about 120° C., about 120° C., about 140° C., or about 150° C.

EXAMPLES

Comparative Example 1

A POSM oxidate was provided which contained about 89 wt. % ethylbenzene, about 9 wt. % ethylbenzene hydroperoxide, with the remaining about 2 wt. % containing acetophenone, methyl benzyl alcohol, carboxylic acids, and phenols. A 250-gram sample of this POSM oxidate was combined with 10.8-g (gram) sample of 3.7 wt. % of NaOH in water, and the mixture was shaken in a separatory funnel. After shaking, the mixture was allowed to separate for 15 min (minutes), and the bottom aqueous layer was removed. A 62-gram sample of deionized water was then added to the separatory funnel and the organic layer was washed by shaking. This mixture was allowed to separate for 15 min, and the bottom aqueous layer was removed. Another 62-gram sample of deionized water was then added to the separatory funnel and the organic layer was again washed by shaking. The resulting mixture was also allowed to separate for 15 min, and the bottom aqueous layer from the second wash was removed. The remaining organic layer was found to contain 0.53 ppm of sodium.

Example 1

A 250-gram sample of the POSM oxidate as used in COMPARATIVE EXAMPLE 1 was combined with 10.8-g (gram) sample of 3.7 wt. % of NaOH in water, and the mixture was shaken in a separatory funnel. After shaking, the mixture was allowed to separate for 15 min (minutes), and the bottom aqueous layer was removed. A 62-gram sample of deionized (DI) water was then added to the separatory funnel and the organic layer was washed by shaking. This mixture was allowed to separate for 15 min, and the bottom aqueous layer was removed. Another 62-gram sample of deionized water that included 2 g of solid $CO_2$ (dry ice) were then added to the separatory funnel with the organic layer, and this mixture was gently agitated and vented as needed to relive excess pressure. The resulting mixture was also allowed to separate for 15 min, and the bottom aqueous layer from the second wash was removed. The remaining organic layer was found to contain 0.20 ppm of sodium.

Comparing the analytical data from COMPARATIVE EXAMPLE 1 and EXAMPLE 1, it is seen that the addition of $CO_2$ reduced the sodium in the organic layer by at least a factor of two. While not intending to be bound by theory, it is thought that the initial caustic treatment converts phenol and ethyl phenols to their sodium salts (sodium phenates). Sodium phenates are partly soluble in the organic layer, making them difficult to completely extract with water from an organic solution and requiring a large volume of water washes. It is thought that the $CO_2$ converts the sodium phenates to phenols plus sodium bicarbonate, and the very polar sodium bicarbonate is very soluble in water and therefore readily removed by water washing. One advantage of $CO_2$ is its ability to convert the sodium phenates to phenols without adding any cation or strong acid which would otherwise act as a catalyst poison downstream. Additionally, $CO_2$ appears to reduce emulsion formation which otherwise complicates the washing process. As sodium carbonate is more hydrophilic than sodium phenate, $CO_2$ helps break the emulsion caused by sodium phenate when converting sodium phenate to phenol and sodium carbonate. Therefore, the disclosed process will reduce the fouling and improve the catalyst life downstream.

Comparative Example 2

A 9.072 kg (20 lb.) sample of EB oxidate was added to a 18.93 L (5 gallon) stainless vessel having a diameter of 22.86 cm (9 inch) and a height of 71.12 cm (28 inch). The vessel included a sight glass mounted at the bottom of the vessel. The EBHP content of the oxidate was 9.2 wt. %. The acidity was 0.0033 meq/gm as measured by titration with KOH. To the vessel was added 570 mL of 1M NaOH in water. A pump was connected to the bottom port so that this mixture could be circulated at a rate of 11.36 L per minute (3 gallons per minute) from bottom to top. The mixing occurred for 10 minutes at 23.89° C. (75° F.) with a nitrogen pad of 0.0689 MPa (10 psig). Then the pump was shut off for 5 minutes. The aqueous layer which formed was drained from the bottom of the vessel using the sight glass to detect the aqueous-organic interface. Then, the pump was turned on again for 10 minutes. The pump was turned off and five minutes later, the remaining aqueous layer was removed from the sight glass at the bottom of the vessel. Then 1.814 kg (4 lb.) of water was then added to the vessel. Next, 5.9 liters per minute of nitrogen was added to the bottom of the sight glass at the bottom of the vessel. The nitrogen feed lasted 20 minutes. Then, after being shut off for 5 minutes, the aqueous layer was drained out. A second 1.814 kg (4 lb.) portion of water was added to the vessel. Again, 5.9 liters per minute of nitrogen was added to the bottom of the sight glass at the bottom of the vessel. The nitrogen feed lasted for 20 minutes. Then, after being shut off for 5 minutes, the aqueous layer was drained out. Finally, a third dose of 1.814 kg (4 lb.) of water was added to the vessel and then mixed with 5.9 liters per minute of nitrogen for 20 minutes. After the nitrogen was shut off for 5 minutes, the third aqueous layer was removed using the sight glass. The remaining organic was cloudy and when analyzed, it was found to contain 2 ppm of sodium by elemental analysis.

Example 2

Another batch of the same EB oxidate was water washed exactly as described in COMPARATIVE EXAMPLE 2 above, except this time the gas used to mix the water was carbon dioxide instead of nitrogen. All of the conditions including amount of oxidate, the amount of water, the gas flow rate and the mixing and settling times were the same. After removal of the final aqueous layer, the remaining organic was clear. When the organic was analyzed for sodium, the result was less than 0.3 ppm sodium.

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

To define the terms used in this disclosure, the definition from the IUPAC Compendium of Chemical Terminology, 2$^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any) whether in enantiomeric or racemic forms, as well as mixtures of stereoisomers, as would be recognized by a skilled artisan, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, a temperature in a liquid-liquid extraction unit is "about 20° C. to about 30° C.". This range should be interpreted as encompassing temperatures of about 20° C. and about 30° C., and further encompasses "about" each of 21° C., 22° C., 23° C., 24° C., 25° C., 26° C., 27° C., 28° C., and 29° C., including any ranges and sub-ranges between any of these values.

Values or ranges may be expressed herein as "about", from "about" one particular value, and/or to "about" another particular value. When such values or ranges are expressed, it will be understood that the embodiments disclosed include the specific value recited. It is also to be understood that the use of the term "about"±10% of the stated value, ±5% of the stated value, or ±3% of the stated value. Applicants reserve the right to proviso out or exclude any individual members of any such group of values or ranges.

Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The publications and patents mentioned in this disclosure are incorporated herein by reference for the purpose of describing the presently described invention.

Embodiments disclosed herein include:

A: A process comprising: providing an alkylaromatic oxidate stream; contacting the alkylaromatic oxidate stream with an aqueous alkali solution to form a mixture, followed by separating the mixture into an aqueous phase and an organic phase; and subjecting the organic phase to one or more washing and separating cycles wherein at least one of the washing and separating cycles comprises washing the organic phase or any subsequent organic phase with water in the presence of carbon dioxide.

B: A process comprising: contacting molecular oxygen with ethylbenzene to form an oxidate stream; contacting the oxidate stream with an aqueous alkali solution to form a mixture, followed by separating the mixture into an aqueous phase and an organic phase; subjecting the organic phase to one or more washing and separating cycles; contacting the ethylbenzene hydroperoxide of a subsequent organic phase with an alkene in the presence of a catalyst to form a reaction mixture comprising an alkene oxide and 1-phenylethanol; and dehydrating the 1-phenylethanol of the reaction mixture to provide styrene; wherein at least one of the washing and separating cycles comprises washing the organic phase or any subsequent organic phase with water in the presence of carbon dioxide.

C: A process comprising: providing an ethylbenzene oxidate stream; contacting the ethylbenzene oxidate stream with an aqueous sodium hydroxide solution to form a mixture, followed by separating the mixture into an aqueous phase and an organic phase; subjecting the organic phase to one or more washing and separating cycles, wherein at least one of the washing and separating cycles comprises washing the organic phase or any subsequent organic phase with water in the presence of carbon dioxide; and directing a portion of any subsequent organic phase to a reactor.

Each of embodiments A, B, and C may have one or more of the following additional elements: Element 1: wherein the alkylaromatic oxidate stream comprises at least one of: (i) an alkylaromatic hydroperoxide, (ii) at least one undesired compound, and (iii) an organic solvent. Element 2: wherein the undesired compound is an acidic compound. Element 3: wherein the undesired compound is an acid. Element 4: wherein the undesired compound is a phenol. Element 5: wherein a washing and separating cycle comprises: washing the organic phase with water to form a subsequent mixture followed by separating the subsequent mixture into a subsequent aqueous phase and a subsequent organic phase. Element 6: wherein the oxidate stream comprises ethylbenzene hydroperoxide. Element 7: wherein the oxidate stream comprises at least one undesired compound. Element 8: wherein the organic phase comprises ethylbenzene hydroperoxide. Element 9: wherein the subsequent organic phase comprises ethylbenzene hydroperoxide. Element 10: wherein the ethylbenzene oxidate stream comprises at least one of: (i) ethylbenzene hydroperoxide, (ii) at least one undesired compound, and (iii) an organic solvent. Element 11: wherein the one or more washing and separating cycles comprises at least two washing and separating cycles, and wherein the first washing and separating cycle comprises washing the organic phase with water in the absence of carbon dioxide. Element 12: wherein the carbon dioxide is provided in the form of gaseous carbon dioxide, dry ice, carbonated water, or supercritical (liquid) carbon dioxide. Element 13: wherein the alkylaromatic comprises ethylbenzene or cumene. Element 14: wherein the aqueous alkali solution comprises an alkali metal hydroxide in a concentration of from about 0.01 wt. % to about 50 wt. %. Elements 15: wherein the aqueous alkali solution comprises sodium hydroxide or potassium hydroxide. Element 16: wherein the contacting step, the one or more washing and separating cycles, or both are conducted at a temperature of from about 10° C. to about 150° C. Element 17: wherein the concentration of alkali metal in the subsequent organic phase is less than the concentration of alkali metal in the subsequent organic phase when the washing and separating cycles are performed in the absence of carbon dioxide. Element 18: wherein the organic solvent comprises an aliphatic or an aromatic hydrocarbon solvent. Element 19: wherein the concentration of the alkylaromatic hydroperoxide in the alkylaromatic oxidate stream is from about 1.0 wt. % to about 40 wt. %. Element 20: wherein the undesired component is selected from the group consisting of: acids, phenols, and combinations thereof. Element 21: wherein the alkene comprises ethylene, propylene, or butylene. Element 22: wherein the concentration of ethylbenzene hydroperoxide in the ethyl benzene oxidate stream is from about 1.0 wt. % to about 40 wt. %.

While certain embodiments of the disclosure have been shown and described, modifications thereof can be made by one skilled in the art without departing from the teachings of this disclosure. The embodiments described herein are exemplary only, and are not intended to be limiting. Many variations and modifications of the disclosure are possible and are within the scope of the same.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the disclosure. The disclosures of all patents, patent applications, and publications cited herein are hereby incorporated by reference.

We claim:

1. A process for treating an alkylaromatic oxidate stream used for alkene oxide production, the process comprising:

providing an alkylaromatic oxidate stream comprising (i) an alkylaromatic hydroperoxide, (ii) at least one undesired compound, and (iii) an organic solvent;

contacting the alkylaromatic oxidate stream with an aqueous alkali solution to form a mixture, followed by separating the mixture into an aqueous phase and an organic phase; and subjecting the organic phase to one or more washing and separating cycles, each cycle comprising washing the organic phase with water to form a subsequent mixture followed by separating the subsequent mixture into a subsequent aqueous phase and a subsequent organic phase, wherein at least one of the washing and separating cycles comprises washing the organic phase or any subsequent organic phase with water in the presence of carbon dioxide, wherein the organic phase and any subsequent organic phase contains the alkylaromatic hydroperoxide, and wherein the organic phase and any subsequent organic phase containing the alkylaromatic hydroperoxide is directed to a reactor.

2. A process according to the claim 1, wherein the one or more washing and separating cycles comprises at least two washing and separating cycles, and wherein the first washing and separating cycle comprises washing the organic phase with water in the absence of carbon dioxide.

3. A process according to claim 1, wherein the carbon dioxide is provided in the form of gaseous carbon dioxide, dry ice, carbonated water, or supercritical (liquid) carbon dioxide.

4. A process according to claim 1, wherein the alkylaromatic comprises ethylbenzene or cumene.

5. A process according to claim 1, wherein the aqueous alkali solution comprises an alkali metal hydroxide in a concentration of from about 0.01 wt. % to about 50 wt. %.

6. A process according to claim 1, wherein the aqueous alkali solution comprises sodium hydroxide or potassium hydroxide.

7. A process according to claim 1, wherein the contacting step, the one or more washing and separating cycles, or both are conducted at a temperature of from about 10° C. to about 150° C.

8. A process according to claim 1, wherein the concentration of alkali metal in the subsequent organic phase is less than the concentration of alkali metal in the subsequent organic phase when the washing and separating cycles are performed in the absence of carbon dioxide.

9. A process according to claim 1, wherein the organic solvent comprises an aliphatic or an aromatic hydrocarbon solvent.

10. A process according to claim 1, wherein the concentration of the alkylaromatic hydroperoxide in the alkylaromatic oxidate stream is from about 1.0 wt. % to about 40 wt. %.

11. A process for the co-production of an alkene oxide and styrene monomer, the process comprising:

contacting molecular oxygen with ethylbenzene to form an oxidate stream comprising ethylbenzene hydroperoxide and at least one undesired compound;

contacting the oxidate stream with an aqueous alkali solution to form a mixture, followed by separating the mixture into an aqueous phase and an organic phase comprising ethylbenzene hydroperoxide;

subjecting the organic phase to one or more washing and separating cycles, each cycle comprising washing the organic phase with water to form a subsequent mixture followed by separating the subsequent mixture into a subsequent aqueous phase and a subsequent organic phase comprising ethylbenzene hydroperoxide;

contacting the ethylbenzene hydroperoxide of the subsequent organic phase with an alkene in the presence of a catalyst to form a reaction mixture comprising an alkene oxide and 1-phenylethanol, wherein the contacting step takes place in a reactor; and dehydrating the 1-phenylethanol of the reaction mixture to provide styrene;

wherein at least one of the washing and separating cycles comprises washing the organic phase or any subsequent organic phase with water in the presence of carbon dioxide.

12. A process according to claim 11, wherein the one or more washing and separating cycles comprises at least two washing and separating cycles, and wherein the first washing and separating cycle comprises washing the organic phase with water in the absence of carbon dioxide.

13. A process according to claim 11, wherein the carbon dioxide is provided in the form of gaseous carbon dioxide, dry ice, carbonated water, or supercritical (liquid) carbon dioxide.

14. A process according to claim 11, wherein the alkene comprises ethylene, propylene, or butylene.

15. A process according to claim 11, wherein the aqueous alkali solution comprises an alkali metal hydroxide in a concentration of from about 0.01 wt. % to about 50 wt. %.

16. A process according to claim 11, wherein the contacting the alkylaromatic oxidate stream with an aqueous alkali solution, the one or more washing and separating cycles, or both are conducted at a temperature of from about 10° C. to about 150° C.

17. A process for removing sodium salts formed in the co-production of propylene oxide and styrene monomer, the process comprising:

providing an ethylbenzene oxidate stream comprising (i) ethylbenzene hydroperoxide, (ii) at least one undesired compound, and (iii) an organic solvent;

contacting the ethylbenzene oxidate stream with an aqueous sodium hydroxide solution to form a mixture, followed by separating the mixture into an aqueous phase and an organic phase;

subjecting the organic phase to one or more washing and separating cycles, each cycle comprising washing the organic phase with water to form a subsequent mixture followed by separating the subsequent mixture into a subsequent aqueous phase and a subsequent organic phase, wherein at least one of the washing and separating cycles comprises washing the organic phase or any subsequent organic phase with water in the presence of carbon dioxide, wherein the organic phase and any subsequent organic phase contains the alkylaromatic hydroperoxide; and directing a portion of any subsequent organic phase to a reactor.

18. A process according to claim 17, wherein the one or more washing and separating cycles comprises at least two washing and separating cycles, and wherein the first washing and separating cycle comprises washing the organic phase with water in the absence of carbon dioxide.

19. A process according to claim 17, wherein the carbon dioxide is provided in the form of gaseous carbon dioxide, dry ice, carbonated water, or supercritical (liquid) carbon dioxide.

20. A process according to claim 17, wherein the aqueous sodium hydroxide solution comprises sodium hydroxide in a concentration of from about 0.01 wt. % to about 50 wt. %.

* * * * *